(12) United States Patent
Delehouze et al.

(10) Patent No.: US 9,995,699 B2
(45) Date of Patent: Jun. 12, 2018

(54) METHOD OF CHARACTERIZING THE THERMAL AGEING OF COMPOSITE MATERIALS, IN PARTICULAR COMPOSITE MATERIALS HAVING AN ORGANIC MATRIX

(71) Applicant: SAFRAN NACELLES, Gonfreville l'Orcher (FR)

(72) Inventors: Arnaud Delehouze, Gonfreville l'Orcher (FR); Emmanuel Piel, Gonfreville l'Orcher (FR); Nicolas Preud'Homme, Gonfreville l'Orcher (FR)

(73) Assignee: SAFRAN NACELLES, Gonfreville l'orcher (FR)

(*) Notice: Subject to any disclaimer, the term of this patent is extended or adjusted under 35 U.S.C. 154(b) by 0 days. days.

(21) Appl. No.: 15/589,049

(22) Filed: May 8, 2017

(65) Prior Publication Data
US 2017/0241924 A1 Aug. 24, 2017

Related U.S. Application Data

(63) Continuation of application No. PCT/FR2015/053313, filed on Dec. 3, 2015.

(30) Foreign Application Priority Data

Nov. 7, 2014 (FR) ...................................... 14 60818

(51) Int. Cl.
*G01N 3/06* (2006.01)
*G01N 3/18* (2006.01)
(Continued)

(52) U.S. Cl.
CPC .............. *G01N 25/02* (2013.01); *B64F 5/60* (2017.01)

(58) Field of Classification Search
CPC ........... G01N 25/4833; G01N 25/4866; G01N 25/18; G01N 25/005; G01N 25/72;
(Continued)

(56) References Cited

U.S. PATENT DOCUMENTS 6,007,240 A * 12/1999 Price ...................... G01N 25/16
374/55
6,491,425 B1 * 12/2002 Hammiche ............. B82Y 35/00
374/10
(Continued)

FOREIGN PATENT DOCUMENTS

JP 5432388 3/1979

OTHER PUBLICATIONS

Grunenfelder, Lessa K., Nutt, Steven R.; Prepreg age monitoring via differential scanning calorimetry, Journal of Reinforced Plastics & Composites, retrieved from jrp.sagepub.com May 22, 2015, pp. 295-302, vol. 31(5), Sage Publications, California.
(Continued)

Primary Examiner — Gail Kaplan Verbitsky
(74) Attorney, Agent, or Firm — Burris Law, PLLC

(57) ABSTRACT

The present disclosure relates to a method of characterizing the thermal ageing of a part made of composite material, in particular a composite material having an organic matrix. The method includes taking from the part a sample of composite material, subjecting the sample to modulated temperature differential calorimetry, determining, from the curve representing the total heat flow component associated with irreversible phenomena, the temperature at which a local extremum appears, this local extremum being characteristic of the thermal ageing, and determining the thermal ageing of the composite material by comparing the temperature at which the local extremum appears with a reference chart.

11 Claims, 3 Drawing Sheets

(51) Int. Cl.
  *G01N 17/00* (2006.01)
  *G01N 25/02* (2006.01)
  *B64F 5/60* (2017.01)

(58) Field of Classification Search
  CPC ........ G01N 3/18; G01K 17/00; G01K 17/006;
    G01K 13/12; G01K 17/02; G01K 17/04;
    G01K 13/00; G01K 17/06
  USPC ........ 148/698, 578; 374/4, 5, 57, 29, 31–39,
    374/10–12, 44, 45; 422/51; 436/147
  See application file for complete search history.

(56) References Cited

U.S. PATENT DOCUMENTS

| | | | | |
|---|---|---|---|---|
| 2006/0076093 | A1* | 4/2006 | Bennon | C22F 1/04 148/698 |
| 2009/0008466 | A1* | 1/2009 | Wardenga | B60H 1/2212 237/28 |
| 2010/0258223 | A1* | 10/2010 | Spyckerelle | C06B 25/34 149/92 |
| 2012/0213246 | A1* | 8/2012 | Honbo | G01N 25/00 374/57 |
| 2014/0323559 | A1* | 10/2014 | Cady | A61K 31/365 514/450 |
| 2014/0334515 | A1* | 11/2014 | Hidalgo | G01N 25/4866 374/10 |

OTHER PUBLICATIONS

Leveque, David et al., Analysis of how thermal aging affects the long-term mechanical behavior and strength of polymer-matrix composites, Composites Science and Technology, 2005, vol. 65, pp. 395-401, available at www.sciencedirect.com, Elsevier Publishing.

Polansky, R. et al., Determination of the thermal endurance of PCB FR4 epoxy laminates via thermal analyses, Polymer Degradation and Stability, 2014, vol. 105, pp. 107-115, available at www.sciencedirect.com, Elsevier Publishing.

International Search Report for International Application PCT/FR20151053313, dated Feb. 17, 2016.

XP-002739979 Showa Electric Wire Co Ltd; Testing Thermal Ageing of Silane Grafted, Polyolefin Coated Wire—By Determining Oxidn. Initiation Temp. by Colorimetric Scanning and Comparing with Initiation Temp. of Control, retrieved from Espacenet Mar. 9, 1979, vol. 1979, Nr. 16. WPI/THOMSON.

* cited by examiner

METHOD OF CHARACTERIZING THE THERMAL AGEING OF COMPOSITE MATERIALS, IN PARTICULAR COMPOSITE MATERIALS HAVING AN ORGANIC MATRIX

CROSS-REFERENCE TO RELATED APPLICATIONS

This application is a continuation of International Application No. PCT/FR2015/053313, filed on Dec. 3, 2015, which claims priority to and the benefit of FR 14/60818 filed on Nov. 7, 2014. The disclosures of the above applications are incorporated herein by reference.

FIELD

The present disclosure relates to a method for characterizing the thermal ageing (thermal aging) of composite materials, in particular composite materials having an organic matrix. The present disclosure is advantageously applied in the aeronautical field, in which the parts made of composite materials are generally subjected to severe thermal stresses.

BACKGROUND

The statements in this section merely provide background information related to the present disclosure and may not constitute prior art.

Among the materials used in aeronautics, the composite materials represent an increasingly important part. The composite material parts of an aircraft are subjected to stresses, in particular thermal stresses, which may lead to the premature aging of the concerned parts.

These stresses concern in particular the propulsion units, namely the turbojet engines and the nacelles surrounding the turbojet engines. Indeed, the members of the turbojet engines and nacelles made of composite materials are subjected to significant thermal variations. For example, in the case of a nacelle, these members are at ambient temperature on the ground, and undergo in flight either very low temperatures (for the members located in the area called cold area of the nacelle), or very high temperatures (for the members located in the area called hot area of the nacelle).

The composite material parts of the nacelles are qualified depending on minimum mechanical characteristics for an exposure at a first given temperature over the service life of the aircraft, and at a second given temperature (a peak temperature, greater than the first temperature) over a short exposure duration accumulated during the lifespan of the aircraft.

In practice, it happens that the composite materials are subjected to temperatures greater than or equal to the second threshold, for a duration causing an unacceptable decrease of the mechanical properties.

It is consequently desirable to be capable of characterizing in an accurate and rapid manner the thermal aging of a composite material member, in particular in order to evaluate the level of loss of the mechanical characteristics of this member.

Methods which allow characterizing thermal aging by evaluating the degree of discoloration of a paint called basecoat are known. However, these are of relative accuracy because the quality of the evaluation is highly dependent on the application of the basecoat (variations in thickness, surface condition, etc.). Furthermore, these methods are naturally applicable only to painted parts, which represent a noteworthy disadvantage in view of the presence of numerous unpainted parts made of composite material.

Moreover semi-destructive control methods are known. These methods require the taking of a material sample whose mechanical characteristics are then analyzed, for example methods of the dynamic mechanical analysis type (also known as DMA, for "Dynamic mechanical analysis"). However, this type of method requires taking a large-sized sample, whose subsequent repair does not fall within the scope of the repairs called "cosmetic repairs".

SUMMARY

The present disclosure provides a method for accurately characterizing the thermal aging of composite material parts, in particular unpainted parts.

For this purpose, the present disclosure relates to a method for characterizing the thermal aging of a composite material part, in particular a composite material having an organic matrix, the method including the steps of:

taking from the part a composite material sample;

subjecting the sample to an analysis by modulated differential scanning calorimetry;

determining, from the curve showing the component of the total heat flow related to the irreversible phenomenon, the temperature at which a local extremum appears, this local extremum being characteristic of the thermal ageing;

determining the thermal aging of the composite material by comparing the temperature at which the local extremum appears with a reference abacus.

Thus, the present disclosure allows determining accurately the actual level of thermal aging of a composite material part, in particular a part on-board an aircraft (for example a part of the propulsion unit). The small sample size desired for the implementation of the method according to the present disclosure allows that the repair of the nacelle member subsequent to the taking falls within the scope of the repairs called "cosmetic repairs" (category defined by the regulations in force). This is a significant advantage because the repairs called cosmetic repairs are far less long and expensive to implement than the repairs called "structural repairs".

In one form, the reference abacus allows determining the residual strength of the composite material depending on the minimum desired mechanical properties.

In one variation, the reference abacus is obtained by comparison between:

first data, resulting from a study allowing determining the decrease in the mechanical properties of the composite material depending on the thermal aging;

second data, resulting from a study allowing determining the thermal aging depending on the temperature at which a local extremum appears.

In one form, the first data are obtained by analysis of a first population of samples having been subjected to different temperatures for different durations, preferably according to a dynamic mechanical analysis method (or DMA).

In one variation, the second data are obtained by modulated differential scanning calorimetry analysis (or mDSC), of a second population of samples, these samples having been subjected to different temperatures for different durations, the different pairs time/temperature of the first population of samples being identical to the pairs time/temperature of the second population of samples.

In one form, the analysis by modulated differential scanning calorimetry is carried out at temperatures lower than 1100° C., preferably lower than 450° C.

In one variation, the volume of the taken sample is lower than or equal to 8 mm³.

In one form, the sample is taken from a part of an aircraft, in particular a part of an aircraft propulsion unit.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1:
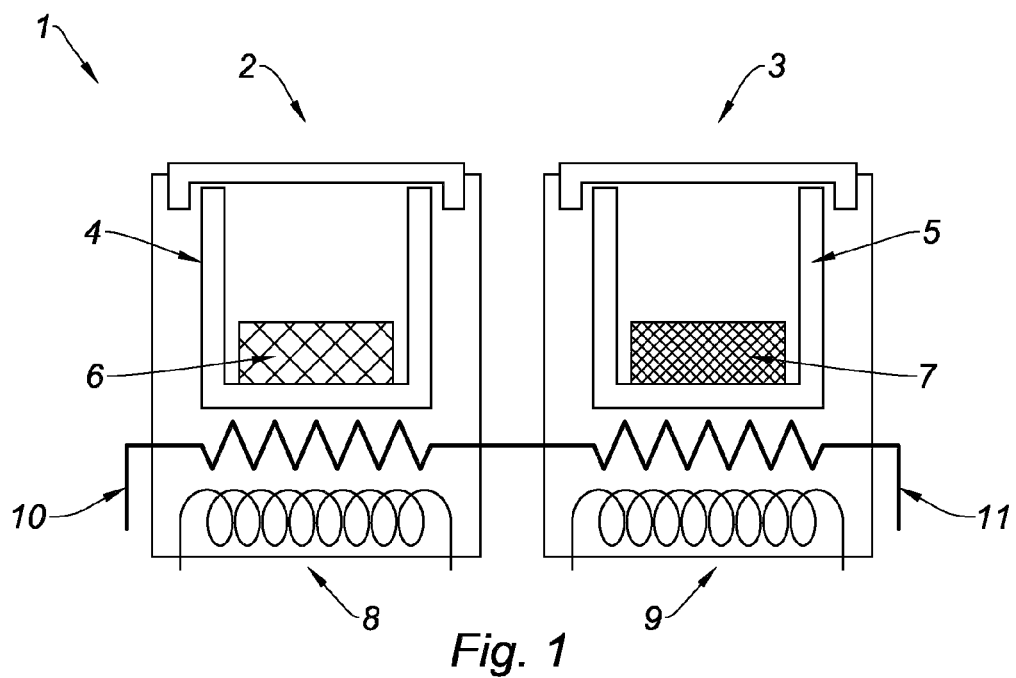
FIG. 1 is a schematic representation of a differential scanning calorimetry device.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

FIG. 1 is a scheme of a differential scanning calorimeter 1. In the example, said differential scanning calorimeter includes two furnaces 2, 3, a first furnace 2 containing in a cupel 4 a reference 6 and a second furnace 3 containing in a cupel 5 a sample 7 to be studied. It will be noted that the cupel 4 of the first furnace 2 can serve as a reference and, in this case, is left empty.

Each one of the furnaces 2, 3 is equipped with respective heating members 8, 9 and the temperatures of the furnaces 2, 3 are measured by resistances 10, 11 (in the example platinum resistances) disposed as close as possible to the cupels 4, 5. Alternatively, the calorimeter may include a single furnace in which are disposed two cupels and the respective temperature measurement resistances thereof.

The calorimeter 1 allows implementing the different techniques of thermal analysis by differential scanning calorimetry, whose particularly modulated differential scanning calorimetry (also called mDSC for "modulated differential scanning calorimetry").

Figure 2:
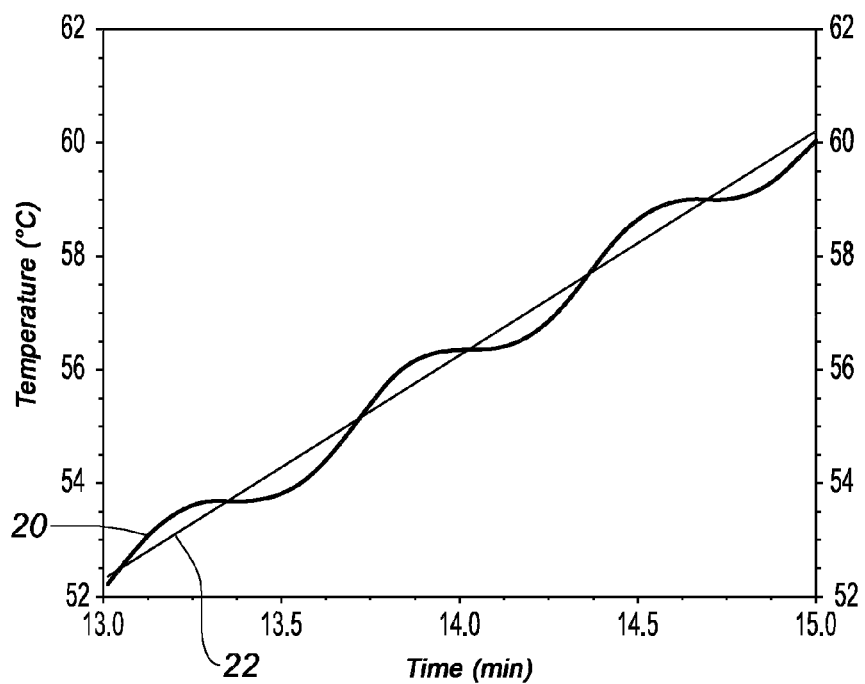
FIG. 2 shows a temperature rise curve used for implementing an analysis by differential scanning calorimetry.

FIG. 2 shows a temperature rise curve typical of an mDSC-type method, which allows measuring the heat flow difference between the sample and the reference, when said sample and reference are subjected to a sinusoidal thermal profile. Thus, it can be seen in FIG. 2 that the curve 20, which represents the temperature rise in the furnaces of the calorimeter, oscillates around a curve 22 corresponding to a linear temperature rise.

By applying a sinusoidal profile such as the sinusoidal profile shown in FIG. 2, the mDSC-type method allows extracting the reversible and irreversible heat flows related to the phenomenon occurring within the sample. Indeed, the sinusoidal modulation of the temperature rise allows discriminating in the total heat flow the components respectively related to the reversible phenomenon and the irreversible phenomenon. This possibility is related to the fact that the average speed of variation of the temperature can be zero while the instantaneous speed is never zero.

Figure 3:
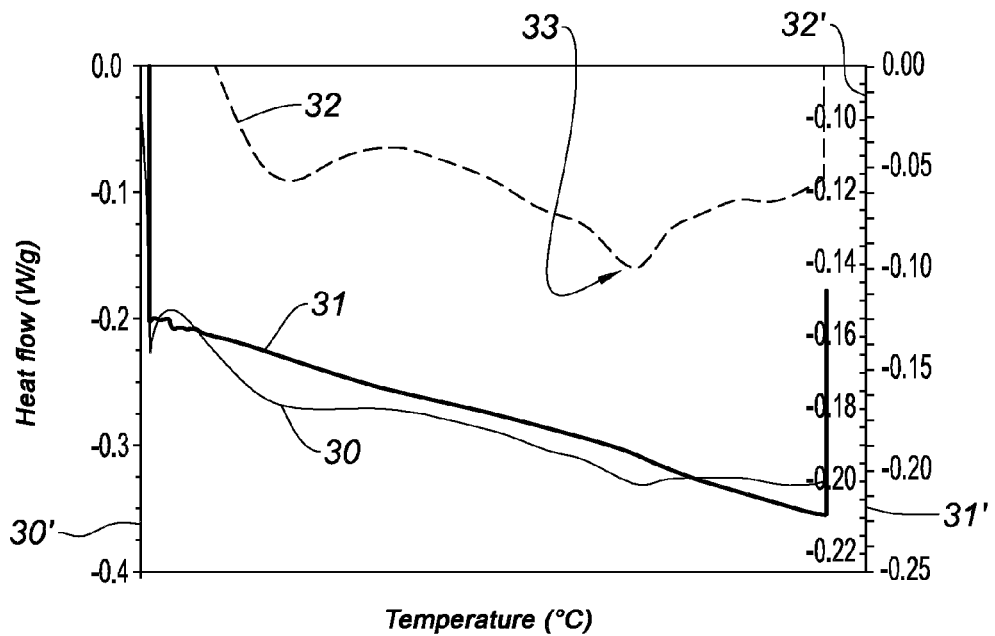
FIG. 3 shows curves obtained during the analysis of a composite material having an organic matrix by modulated differential scanning calorimetry.

FIG. 3 shows a thermogram obtained according to an mDSC-type method. The graph of FIG. 3 shows in ordinate the heat flow (in W/g). A first curve 30 (associated with a first graduation 30') represents the total heat flow. A second curve 31 (associated with a second graduation 31') represents the component of the total heat flow related to the reversible phenomenon. Finally, a third curve 32 (associated with the graduation 32') represents the component of the total heat flow related to the irreversible phenomena.

In the context of the present disclosure, the exploitation of the thermogram of FIG. 3, and mainly of the component related to the irreversible phenomenon, allows observing a peak 33. The peak 33 is related to an endothermic phenomenon whose appearance temperature is associated with the effect of the thermal aging of the analyzed material. In the context of the present disclosure, it will be noted that it is particularly advantageous to carry out calorimetry analyzes at temperatures lower than 1100° C., and more particularly at temperatures lower than 450° C. Indeed, by remaining below this threshold, the influence of the reinforcing fibers of the composite material is limited in the observed thermal phenomena. However, the thermal aging of a composite material on-board an aircraft generally results mainly from the thermal aging of the matrix (in general a resin). It is therefore pertinent that the thermal analysis of the composite material is performed so as to take into account only the thermal aging of the matrix.

Figure 4:
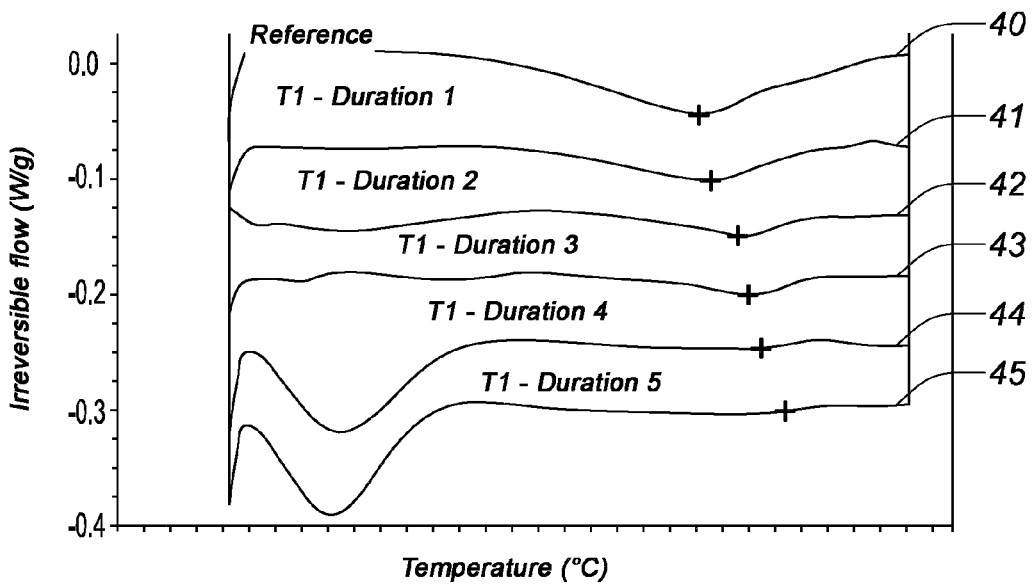
FIG. 4 shows curves of the irreversible heat flow, obtained for different samples.

In accordance with the present disclosure, the analysis by modulated differential scanning calorimetry of samples of a composite material having an organic matrix, including a reference (generally simply constituted by a cupel left empty) and samples having been subjected beforehand to different pairs temperature/duration, allows characterizing the level of thermal aging. FIG. 4 shows, for example, the curves of the "irreversible" heat flow obtained for the reference sample (curve 40) and for samples having been exposed to a temperature T1, respectively for a duration D1, D2, D3, D4 and D5 (curves 41, 42, 43, 44, 45). The comparison of the different curves shown in FIG. 4 allows noticing the evolution of the peak characterizing the thermal aging (peak identified on each curve of FIG. 4 by a cross). It is noticed that for a given temperature T1, when the duration of exposure increases, the energy represented by the peak decreases, while the appearance temperature of the peak increases. Similar evolutions are also observed for an exposure to different temperatures for a given duration.

Figure 6:
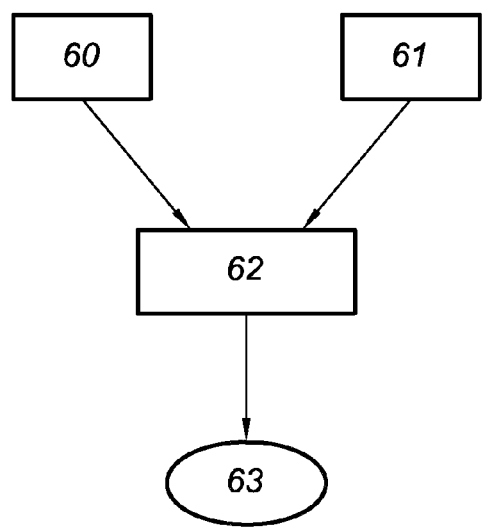
FIG. 6 is a diagram showing the steps allowing constructing a reference abacus in accordance with the present disclosure.

As shown in FIG. 6, the analysis of samples by mDSC is carried out for certain number of pairs time/temperature (step 60) and the results obtained are compared (step 62) with the data of a reference study determining the deterioration of the mechanical properties depending on the thermal aging. This comparison allows extracting an abacus 63 giving the residual mechanical strength of the concerned composite material depending on the appearance temperature of the peak shown in particular in FIG. 4. The data concerning the thermal aging of the reference study have been obtained by any suitable method (step 61), for example by means of DMA-type tests on a population of samples having been subjected to the same pairs time/temperature as the population of samples tested by mDSC.

Figure 5:
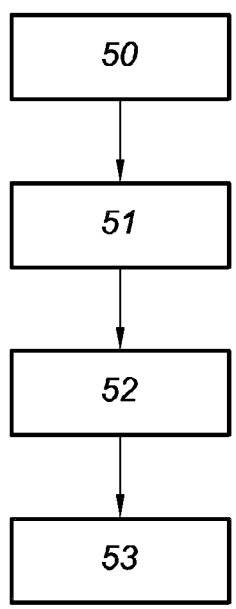
FIG. 5 is a diagram showing the steps allowing determining the thermal aging of a composite material part, in accordance with the present disclosure.

The abacus 63 obtained in accordance with the present disclosure is directly usable by the staff in charge of the maintenance. Thus, it becomes possible, thanks to this abacus, to accurately characterize the level of aging of the composite material constituting a part on-board an aircraft (in particular a part located in the propulsion unit). As shown in FIG. 5, it is sufficient for the staff to take a sample from the concerned part (step 50) and to subject it to a calorimetry analysis (step 51), so as to determine the temperature of the reference peak described hereinabove (step 52). The appearance temperature of the reference peak is then compared with the reference abacus 63, which allows deducing the level of thermal aging of the taken sample (step 53).

The present disclosure allows characterizing the thermal aging of a composite material part from a very small-sized sample (about 8 cubic millimeters), so that the subsequent repair to the taking of a sample falls within the scope of the repairs called cosmetic repairs. Furthermore, the method according to the present disclosure is applicable to the painted parts as well as the unpainted parts.

Although the present disclosure has been described relating to a particular variation, it is obvious that it is in no way limited thereto and that it comprises all the technical equivalents of the means described as well as the combinations thereof if said combinations fall within the scope of the present disclosure.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A method for characterizing the thermal ageing of a part made of a composite material, the method including the steps of:
    taking a sample from the part;
    subjecting the sample to analysis by modulated differential scanning calorimetry;
    determining from a curve representing a component of a total heat flow related to an irreversible phenomenon, a temperature at which a local extremum appears, the local extremum being characteristic of the thermal ageing; and
    determining a level of the thermal ageing of the composite material by comparing the temperature at which the local extremum appears with a reference abacus.

2. The method according to claim 1, wherein the reference abacus determines a reduced strength of the composite material depending on minimum mechanical properties.

3. The method according to claim 1, wherein the reference abacus is obtained by a comparison between:
    a first data, resulting from a study determining a decrease in mechanical properties of the composite material depending on the thermal ageing; and
    a second data, resulting from a study determining the thermal ageing depending on the temperature at which a local extremum appears.

4. The method according to claim 3, wherein the first data are obtained by analysis of a first group of samples having been subjected to different temperatures for different durations.

5. The method according to claim 3, wherein the first data are obtained by a dynamic mechanical analysis method.

6. The method according to claim 4, wherein the second data are obtained by modulated differential scanning calorimetry analysis of a second group of samples, the samples having been subjected to different temperatures for different durations, the different temperatures and durations of the first group of samples being identical to the temperatures and durations of the second group of samples.

7. The method according to claim 1, wherein the modulated differential scanning calorimetry analysis is carried out at temperatures lower than 1100° C.

8. The method according to claim 1, wherein the modulated differential scanning calorimetry analysis is carried out at temperatures lower than 450° C.

9. The method according to claim 1, wherein a volume of the sample is lower than or equal to 8 mm$^3$.

10. The method according claim 1, wherein the sample is taken from a part of an aircraft.

11. The method according claim 10, wherein the sample is taken from a part of an aircraft propulsion unit.

* * * * *